United States Patent

Chao et al.

[11] Patent Number: 5,706,088
[45] Date of Patent: Jan. 6, 1998

[54] POLARIZER-SAMPLE-ANALYZER INTENSITY QUOTIENT ELLIPSOMETRY

[75] Inventors: Yu-Faye Chao; Chi-Shing Wei, both of Hsinchu Hsien; Wen-Chi Lee, I-Lan, all of Taiwan

[73] Assignee: National Science Council, Taipei, Taiwan

[21] Appl. No.: 603,779

[22] Filed: Feb. 20, 1996

[51] Int. Cl.⁶ ................................................ G01N 21/21
[52] U.S. Cl. ................................................ 356/369
[58] Field of Search ........................... 356/369, 364, 356/365, 366, 367

[56] References Cited

U.S. PATENT DOCUMENTS

| | | | |
|---|---|---|---|
| 4,030,836 | 6/1977 | Smith | 356/369 |
| 4,516,855 | 5/1985 | Korth | 356/369 |

OTHER PUBLICATIONS

McCrackin et al., J. Res. Natl. Bur. Stand., vol. 67A, No. 4, pp. 363–377, Jul.–Aug. 1963.

Kawabata, J. Opt. Soc. Am. A/vol. 1, No. 7, pp. 706–710, Jul. 1984.

Meyer et al., J. Applied Physics, vol. 38, No. 9, pp. 3682–3684 (Aug. 1967).

Collins, Rev. Sci. Instrum. 61(8), pp. 2029–2062 (Aug. 1990).

*Primary Examiner*—Richard A. Rosenberger

[57] ABSTRACT

A polarizer-sample-analyzer intensity quotient ellipsometer and ellipsometric technique is disclosed which includes: a polarized light source, including a light source and a polarizer, for providing polarized light; and a detecting device, including an analyzer and a photodetector. The ellipsometer successively measures three intensities of polarized light emitted by the polarized light source and reflected by the sample being measured with the azimuth angle of the polarizer rotated to ±45° with respect to a plane of incidence and the azimuth angle of the analyzer successively rotated to 0°, 60°, and 120°. With these three measurements, the ellipsometric parameters $\psi$ and $\Delta$ can be deduced. The invention also calculates deviations in the azimuth angles of the polarizer and analyzer with respect to a plane of incidence by utilizing two intensity quotients under two incident angles to be equal after roughly adjusting azimuth angles of the polarizer and the analyzer.

3 Claims, 1 Drawing Sheet

POLARIZER-SAMPLE-ANALYZER INTENSITY QUOTIENT ELLIPSOMETRY

BACKGROUND OF THE INVENTION

1. Field of the Invention

The present invention relates to a method and apparatus for measuring ellipsometric parameters. More particularly, this invention relates to a method and apparatus for measuring ellipsometric parameters by using a polarizer-sample-analyzer intensity quotient.

2. Description of Prior Art

It is known that ellipsometric parameters $\psi$ and $\Delta$ can be used to deduce the optical constants (e.g., complex refractive index and film thickness) of a sample.

The basic requirement in ellipsometric measurement is to precisely calibrate all of the azimuth angles of optical components with respect to the plane of incidence. This has been widely studied in both null and rotating-analyzer ellipsometry. The accuracy of the azimuth angle of the polarizer and analyzer has rarely been discussed in static photometric ellipsometry (which is often used in remote sensing as a polarimeter). The spatial polarization distribution of this technique is of primary interest rather than the polarization changes through a medium.

Using a measurement technique known as ellipsometry, one can deduce the optical properties of materials by measuring changes the polarization state of light reflected by the sample. The ellipsometric parameters $\psi$ and $\Delta$ are defined as $\tan \psi e^{i\Delta} = r_p/r_s$, where $r_p$ and $r_s$ are reflection coefficients of P-polarized and S-polarized components of the beam, respectively, in the plane of incidence (hereinafter referred to as POI). In previous studies, the ellipsometric parameters $\psi$ and $\Delta$ are measured and used to deduce the optical parameters, such as complex refractive index and film thickness of the sample.

There are two basic types of prior-art ellipsometers, that is, null ellipsometers and photometric ellipsometers. Well-calibrated compensators are usually required for both the null and photometric ellipsometers to obtain an accurate ellipsometric parameter $\Delta$. Therefore, the null and photometric ellipsometers are also called a PCSA (Polarizer-Compensator-Sample-Analyzer) system.

However, all ellipsometers measure the ellipsometric parameters of reflective light by using polarization angles of optical components in the system. Therefore, the measurement precision of an ellipsometer depends on whether the polarization angles of the optical components are collimated and accurately aligned with respect to the POI.

McCrackin et al. discloses a method for correcting the polarization angle of a null ellipsometer in J. Res. Natl. Bur. Std, 67A, 363 (1963), which uses an absolute least luminance method to collimate each component in the system to the POI to within 0.02°, and measures ellipsometric parameters by a 4-zone method. This method of finding the least luminance, in addition to wasting time, requires a detector having high sensitivity to detect the null. It also requires utilization of a lock-in amplifier to eliminate the effect of noises produced therein.

Another prior-art ellipsometer referred to by R. W. Collins is a photometric ellipsometer which is gradually taking the place of null ellipsometers. The ellipsometer disclosed by Collins measures ellipsometric parameters with a lock-in amplifier or Fourier transform because it measures periodic luminance.

Accordingly, both of the above conventional ellipsometers require an expensive compensator having dispersion characters that affect the result, as well as a detecting system with high sensitivity and fast response. These conventional ellipsometers also require precise alignment of the optical components.

Furthermore, by applying the least-squares method to a set of 36 data in a cycle, Meyer et al. extracts the ellipsometric parameters from the measured intensity distribution using a simple PSA (polarizer-sample-analyzer) ellipsometer as disclosed in J. Appl. Phy. 38(1967) 3682. The intensity distribution of the reflected, elliptically polarized light can be determined by measuring three radiances through three linear polarizers each spaced 60° from one another. For rotating-analyzer-ellipsometry, Kawabata suggests a technique disclosed in JOSA A. 1(1984) 706 to obtain the small azimuthal deviation of the polarizer by carrying out the measurements at two 90° different azimuths of the polarizer.

SUMMARY OF THE INVENTION

Accordingly, it is the primary object of the present invention to provide a PSA (Polarizer-Sample-Analyzer) intensity quotient ellipsometric method and apparatus, which does not require a compensator (thereby preventing dispersion when used to measure various wavelengths) and does not require precise optical component alignment.

It is another object of the present invention to provide a PSA intensity quotient ellipsometer, which can calculate ellipsometric parameters by measuring luminance of three radiances according to the present invention, thereby not requiring a detecting system having a fast response.

To achieve these objects, the invention systematically aligns the polarizer and analyzer to the surface of reflection, takes a pair of three intensity measurements with the polarizer azimuth angle set at ±45°. This technique uses only 3×2 intensity measurements instead of 36×2 intensity measurements to obtain the ellipsometric parameters. The results are comparable to those obtained by the classical null ellipsometry. The present invention also determines the azimuthal deviation of the polarizer with the same set of data.

In addition to a typical $SiO_2$ thin film, an optically thick metal film (Pt) on a silicon substrate is measured for a bulk model. Both measurements are compared with those measured by a two-zone fixed angle null ellipsometer (Rudolph: AutoEL II).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following detailed description, given by way of example and not intended to limit the invention solely to the embodiments described herein, will best be understood in conjunction with the accompanying drawings in which.

DETAILED DESCRIPTION OF THE PREFERRED EMBODIMENTS

Figure 1:
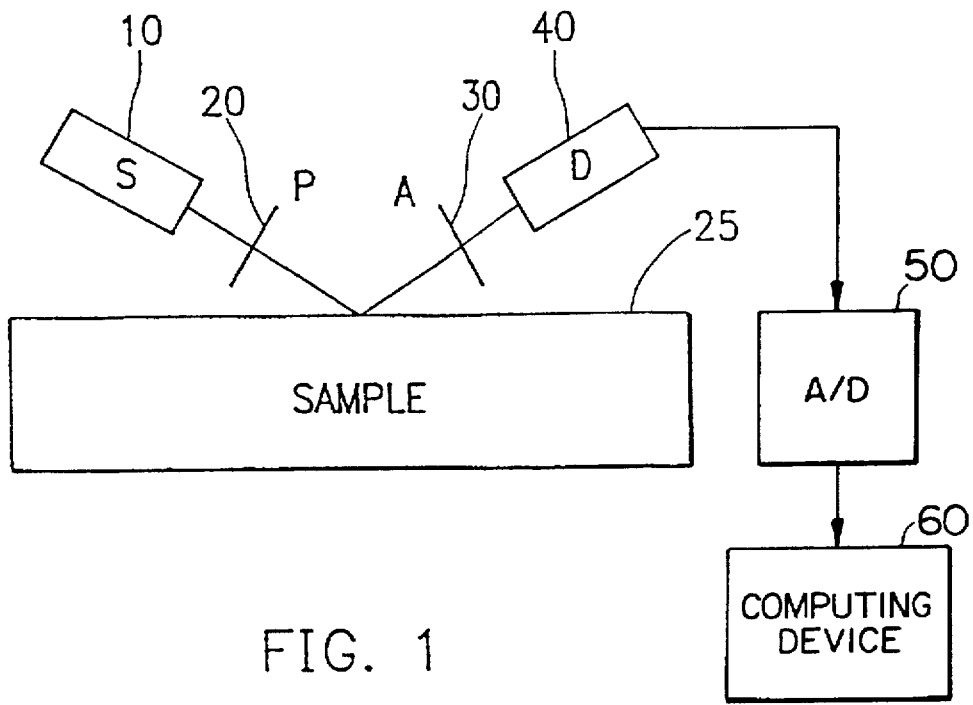
FIG. 1 is a diagram illustrating the architecture of the polarizer-sample-analyzer intensity quotient ellipsometer according to the present invention.

Referring to FIG. 1, the polarizer-sample-analyzer intensity quotient ellipsometer of the present invention includes: a light source device 10, a polarizer 20, an analyzer 30, a detector device 40, an A/D converter 50, and a computing device 60. A sample 25 to be measured is placed between the polarizer 20 and the analyzer 30.

To test the preferred embodiment of the preset invention, the sample includes a $SiO_2$ thin film and a Pt thin film having a thickness of about 500 Å, which are both formed on a Si substrate. Moreover, to compare the measured results with the results of the prior-art null ellipsometry (i.e., Rudolph:AutoEl II), the incident angle is set to 70°±0.02°.

The light emitted from the light source device 10, such as a HeNe laser, passes through the polarizer 20, in which the azimuth angle P of the polarizer 20 with respect to the POI of the sample 25 being measured is set to ±45°.

The analyzer 30 is mounted on a turntable controlled by a step motor (not shown in the drawing). Next, six sets of measurements are taken and then processed. One of the sets of measurements includes 36 data measured during the whole cycle to verify the theoretical inference. Each of the other five sets of measurements includes 3 data which are measured while the azimuth angle A of the analyzer is 0°, 60° and 120°. All of the intensities are measured by a detector 10 such as a power meter (i.e., Newport 818-SL) and digitized by an A/D converter 50 such as a multimeter (Keithley 195A) and then stored and processed by a computing device 60 such as a personal computer.

One of the sets of measurements can be used to deduce the ellipsometric parameters $\psi$ and $\Delta$, and further to deduce the optical characteristics of the sample, such as its complex refractive index.

The deduction process of the ellipsometric parameters is given below: as described above, the ellipsometric parameters $\psi$ and $\Delta$ can be defined as $$\tan \psi e^{i\Delta} = r_p r_s$$

The light intensity measured by the detector 40 in the PSA system can be represented as $$I(P,A) = I_o [\sin^2 P \sin^2 A + \tan^2 \psi \cos^2 P \cos^2 A + (\frac{1}{2}) \tan \psi \cos \Delta \sin 2P \sin 2A] \quad (1)$$

where, P and A are azimuth angles of the polarizer 20 and the analyzer 30, respectively, $I_o$ is the intensity of the measured beam. At this time, if the azimuth angle P of the polarizer 20 with respect to the POI of the sample is set to 45° then the equation (1) can be simplified as $$J(A) = 0.5 I_o [\sin^2 A + \tan^2 \psi \cos^2 A + \tan \psi \cos \Delta \sin 2A] \quad (2)$$

The equation (1) can also be represented as $$J(A) = L \cos^2(A - \beta_0) + T \sin^2(A - \beta_0), \quad (3)$$

where $\beta_0$ represents an auxilliary angle between major axis L and the plane of incidence (See FIG. 2) By comparing the equations (2) and (3), the following can be obtained $$\tan 2\beta_0 = -\cos \Delta \tan \psi \quad (4)$$

and $$\tan 2\psi = (1 - R \cos 2\beta)/(1 + R \cos 2\beta) \quad (5)$$

where, the normalized ratio R of the characteristic lengths L and T (FIG. 2) is $R=(L-T)/(L+T)$. From the equation (3), L, T and $\beta_0$ can be computed by plugging in three intensity measurements. That is, three intensities are measured while the azimuth of the analyzer is 0°, 60° and 120°. The result is as follows:

$$\tan 2\beta_0 = \sqrt{3}[J(60) - J(120)]/[2J(0) - J(60) - J(120)] \quad (6)$$

and $$R \cos 2\beta_0 = [2J(0) - J(60) - J(120)]/[J(0) + J(60) + J(120)] \quad (7)$$

Substituting equations (6) and (7) into equations (4) and (5), the ellipsometric parameters $\psi$ and $\Delta$ can be obtained.

To obtain more accurate values of the ellipsometric parameters the invention compensates for deviations ($\alpha$) in the polarizer azimuth angle P. If the azimuth angle P of the polarizer has a small deviation $\alpha$, for $P = \pm 45° + \alpha$, the equation (1) can be rewritten as $$J(A) = 0.5 I_o \{\sin^2 A + \tan^2 \psi \cos^2 A \pm [(\sin^2 A - \tan^2 \psi \cos^2 A) \sin 2\alpha + \tan \psi \cos \Delta \sin 2A \cos 2\alpha]\} \quad (8)$$

Similar to the inference of the equation (3), while $P = 45° + \alpha$ $$\tan^2 \psi = (1 - \sin 2\alpha)(1 - R \cos 2\beta_0)/(1 + \sin 2\alpha)(1 + R \cos 2\beta_0) \quad (9)$$

and while $P = -45° + \alpha$ $$\tan^2 \psi = (1 + \sin 2\alpha)(1 - R' \cos 2\beta')/(1 - \sin 2\alpha)(1 + R' \cos 2\beta') \quad (10)$$

where, R' and $\beta'$ are corresponding coefficients of the equation (3). By multiplying equation (9) and equation (10), one can infer tan $\psi$ is independent of the deviation $\alpha$ of the azimuth angle P of the polarizer. At the same time, by dividing the equation (9) into the equation (10), the value of $\alpha$ can be calculated. Repeating the process of deducing the equation (4), it can be obtained that tan $\beta_0 = -\tan \beta'$ while $\alpha$ equals 0. Therefore, by taking $\beta_{av} = (180 - \beta + 62_0)/2$, a more accurate $\Delta$ value can be obtained.

Figure 2:
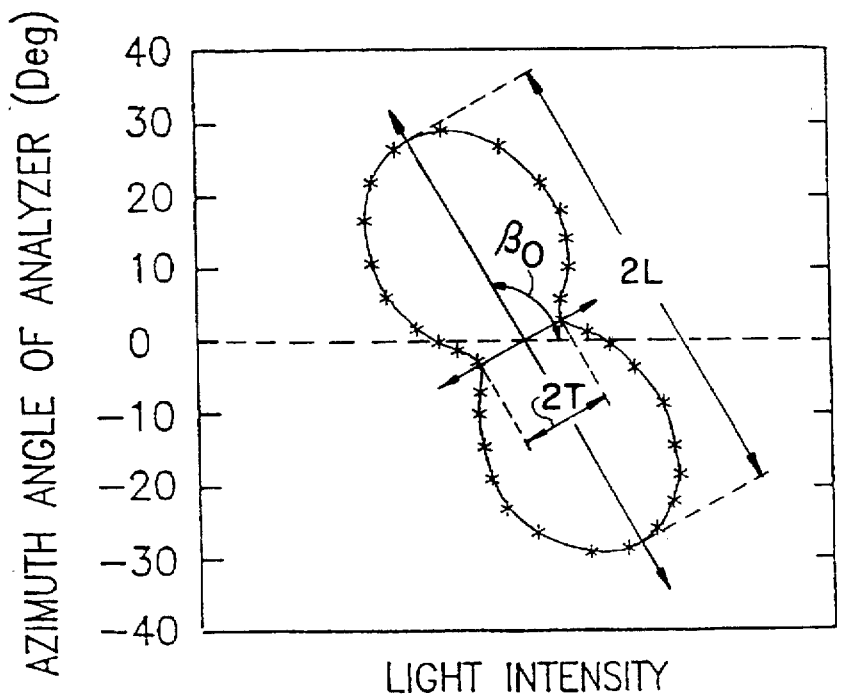
FIG. 2 is a diagram illustrating the intensity distribution measured by the polarizer-sample-analyzer intensity quotient ellipsometer according to the present invention.

The values of tan $\psi$ and cos $\Delta$ are deduced from equations (3) to (7) by utilizing three intensity measurements. Substituting the deduced values into equation (2), the intensity distribution is plotted in a polar coordinate as shown in FIG. 2. This figure illustrates that the calculated intensity distribution (represented by a solid line) matches very well with the measured intensities (represented by star-sign), and suggests that three measurements are sufficient to extract the ellipsometric parameters.

In addition, the ellipsometric parameters measured by the PSA photometric ellipsometer can be improved by measuring intensities with a pair of polarizer azimuths angles differing by 90°. More particularly, the invention systematically aligns the polarizer and the analyzer to the POI of the sample by applying the following steps:

(a) measure an intensity $I_{a1}$ at a first incident angle while the polarizer azimuth angle P is rotated to 45° and the analyzer azimuth angle A is at the aligned position, (b) measure an intensity $I_{a2}$ at the first incident angle while the polarizer azimuth angle A is rotated to 45° and the analyzer azimuth angle A is rotated to 90°, (c) measure an intensity $I_{b1}$ at the first incident angle while the polarizer azimuth angle P is rotated to −45° and the analyzer azimuth angle A is at the aligned position, (d) measure an intensity $I_{b2}$ at the first incident angle while the polarizer azimuth angle P is rotated to −45° and the analyzer azimuth angle is rotated to 90°, (e) obtain the azimuthal deviations $\alpha$ and $\beta$ of the polarizer and the analyzer azimuth angles, respectively by deducing the positions of the polarizer and the analyzer corresponding to the plane of incidence according to intensity quotients $\Gamma_a$ and $\Gamma_b$, respectively defined by $\Gamma_a = I_{a1}(\pi/4+\alpha,\beta)/I_{a2}(\pi/4+\alpha,\pi/2+\beta) = \tan^2\psi = 2[2\tan^2\psi\cdot\alpha - \sec^2\psi\cdot\tan\psi\cdot\cos\Delta\cdot\beta]$ $\Gamma_b = I_{b1}(-\pi/4+\alpha,\beta)/I_{b2}(-\pi/4+\alpha,\pi/2+\beta) = \tan^2\psi + 2[2\tan^2\psi\cdot\alpha - \sec^2\psi\cdot\tan\psi\cdot\cos\Delta\cdot\beta]$ hence, while $\Gamma_a = \Gamma_b$, $[2\tan^2\psi\cdot\alpha - \sec^2\psi\cdot\tan\psi\cdot\cos\Delta\cdot\beta] = 0$ (f) repeating the measuring steps and the obtaining the azimuthal deviations $\alpha$ and $\beta$ step for a second incident angle, so that $\alpha$ and $\beta$ can be calculated by solving simultaneous equations for the first and second incident angles.

In summary, there are three major contributions of the invention:

(a) the systematic alignment technique which is used to align the polarizer and the analyzer to the POI for two incident angles (one is larger than the principle angle which equals to the Brewster angle for nonabsorbent materials and the other is less than the principle angle) includes the steps of adjusting the polarizer around 45° to the incident plane while the incident angle is less than the principle angle, then rotating the analyzer around 0°, measuring the intensity distribution $I_{a1}$, then rotating the analyzer 90°, and measuring the intensity distribution $I_{a2}$, therefore obtaining the intensity ratio $\Gamma_a$, thereafter repeating the above procedure for the polarizer is adjusted around −45° to the incident plane to obtain $I_{b1}$, $I_{b2}$, and $\Gamma_b$, then repeating all of the above procedures for an incident angle larger than the principle angle, solving the equations for $\Gamma_a$ and $\beta_b$ to obtain $\alpha$ and $\beta$, so that the polarizer and the analyzer can be aligned to the incident plane;

(b) using three intensity measurements I(0), I(60) and I(120) to calculate the two auxiliary parameters $\tan 2\beta_0$ and $R\cos 2\beta_0$ for deducing the ellipsometric parameters $\psi$ and $\Delta$ at P=45°, (c) performing the same procedure for P=−45°, then deducing the deviations $\alpha$, $\beta$ from the measurements and correcting the error in the ellipsometric parameters that may occur due to the deviations.

In the following Tables 1 and 2, the measured results of the present invention are compared with those measured by a two-zone null ellipsometer.

TABLE 1

|  | Ψ | Ψ | Δ | Δ | Ψ | Δ | α |
|---|---|---|---|---|---|---|---|
| Azimuth of P | +45° | −45° | +45° | −45° | improved | improved |  |
| 1 | 32.839 | 34.348 | 125.584 | 120.702 | 33.589 | 123.116 | 0.093 |
| 2 | 32.845 | 34.346 | 125.571 | 120.728 | 33.591 | 123.123 | 0.095 |
| 3 | 32.839 | 34.347 | 125.577 | 120.699 | 33.588 | 123.110 | 0.093 |
| 4 | 32.839 | 34.344 | 125.582 | 120.714 | 33.587 | 123.121 | 0.094 |
| 5 | 32.845 | 34.348 | 125.570 | 120.702 | 33.592 | 123.109 | 0.092 |
| Mean | 32.840 | 34.346 | 125.579 | 120.711 | 33.588 | 123.118 | 0.094 |
|  | (0.003) | (0.002) | (0.005) | (0.011) | (0.002) | (0.005) | (0.002) |
| Vary P by 1° | 31.856 | 35.237 | 125.476 | 120.891 | 33.526 | 123.47 | 1.163 |
|  | (0.007) | (0.005) | (0.03) | (0.02) | (0.003) | (0.02) | (0.003) |
| Null Rudolph AutoEL II |  |  |  |  | 33.58 (0.02) | 123.34 (0.04) | * |

TABLE 2

|  | Ψ | Ψ | Δ | Δ | Ψ | Δ | α |
|---|---|---|---|---|---|---|---|
| Azimuth of P | +45° | −45° | +45° | −45° | improved | improved |  |
| 1 | 51.342 | 50.578 | 80.232 | 81.378 | 50.960 | 80.80 | −0.025 |
| 2 | 51.344 | 50.577 | 80.240 | 81.379 | 50.960 | 80.81 | −0.029 |
| 3 | 51.334 | 50.578 | 80.249 | 81.389 | 50.956 | 80.82 | −0.022 |
| 4 | 51.333 | 50.578 | 80.239 | 81.394 | 50.956 | 80.82 | −0.017 |
| 5 | 51.344 | 50.578 | 80.240 | 81.378 | 50.961 | 80.81 | −0.028 |
| Mean | 51.344 | 50.575 | 80.243 | 81.385 | 50.957 | 80.82 | −0.022 |
|  | (0.005) | (0.006) | (0.009) | (0.02) | (0.004) | (0.02) | (0.005) |
| Null Rudolph AutoEL II |  |  |  |  | 50.96 (0.01) | 81.23 (0.02) | * |

These Tables indicate that the method of the present invention, requiring no compensator, can still achieve less than 0.1% errors for both ellipsometric parameters. Even if the azimuth angle of polarizer P deviates by 1° the ellipsometric parameters are only off by 0.2% by utilizing the techniques of this invention.

In general, the value of Δ measured by the PSA technique is smaller than that found by the null ellipsometer. Since the highly absorbing Pt film can be considered as a bulk medium, one can deduce the complex refractive index from the measured ellipsometric parameters; the results obtained are 2.065-i3.924(PSA) and 2.089-i3.955(null). The measurement of ψ is 40.96° for an incident angle of 45°, and the refractive index determined from the intersection of two iso-tan ψ curves as used in Appl. Opt. 20(1981)3961, by P. Tomaselli et al. is 2.075-i3.937. The deduced refractive indices from various methods are all within 1% of each other. The thickness of the $SiO_2$/Si thin film deduced from the ellipsometric parameters is 1133 Å by Null.

This simple PSA ellipsometer can be easily converted into a transmission ellipsometer for measuring an anisotropic medium. Since no compensator is required in this simple device, one can use it for spectroscopic ellipsometric analysis to avoid the dispersion problem associated with a compensator.

While the present invention has been particularly shown and described with reference to a preferred embodiment, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A method for measuring ellipsometric parameters of a sample by using a polarizer-sample-analyzer intensity quotient, comprising the steps of:

(i) providing a sample to be measured;

(ii) providing a polarizer and an analyzer above the sample;

(iii) projecting a light beam through the polarizer to obtain a linearly polarized light beam;

(iv) reflecting the linearly polarized light beam off of the sample;

(v) projecting the reflected light beam through the analyzer;

(vi) systematically aligning the polarizer and the analyzer to an aligned position corresponding to a plane of incidence of the sample;

(vii) rotating an azimuth angle of the polarizer to 45° with respect to the plane of incidence;

(viii) measuring the intensity of the polarized light beam that has passed through the analyzer;

(ix) rotating an azimuth angle of the analyzer to 60°;

(x) measuring the intensity of the polarized light beam that has passed through the analyzer;

(xi) rotating the azimuth angle of analyzer to 120°;

(xii) measuring the intensity of the polarized light beam that has passed through the analyzer;

(xiii) deducing ellipsometric parameters $\psi$ and $\Delta$ of the simple according to the following process by utilizing the intensities measured in steps (viii), (x) and (xii), wherein the ellipsometric parameters $\psi$ and $\Delta$ can be defined as $$\tan \psi e^{i\Delta} = r_p/r_s,$$

where $r_p$ and $r_s$ are reflection coefficients of p polarized and s polarized light, respectively, and the intensities measured in steps (viii), (x) and (xii) are represented as $$J(A) = 0.5 I_0 [\sin^2 A + \tan^2 \psi \cos^2 A + \tan \psi \cos \Delta \sin 2A]$$

and as $$J(A) = L \cos^2(A-\beta_0) + T \sin^2(A-\beta_0),$$

where A represents a rotation angle of the analyzer and $I_0$ is the intensity being measured and $\beta_0$ is an auxiliary angle between a major axis L and the plane of incidence, wherein $R=(L-T)/(L+T)$ where R is a normalized ratio between the major axis L and a minor axis T, substituting the three intensities respectively measured in the steps (viii), (x) and (xii) to the following equations, $$\tan 2\beta_0 = \sqrt{3}[J(60) - J(120)]/[2J(0) - J(60) - J(120)]$$

and $$R \cos 2\beta_0 = [2J(0) - J(60) - J(120)]/[J(0) + J(60) + J(120)]$$

then, after calculating R and $\beta_0$, substituting R and $\beta_0$ into the following equations to calculate the ellipsometric parameters $\Delta$ and $\psi$ $$\tan 2\beta_0 = -\cos \Delta \tan \psi$$

and $$\tan 2\psi = (1-R \cos 2\beta_0)/(1+R \cos 2\beta_0).$$

2. The method for measuring ellipsometric parameters as claimed in claim 1, further comprising the step of:

replacing the equation for J(A), by the following equation $$J(A) = 0.5 I_0 \{ \sin^2 A + \tan^2 \psi \cos^2 A \pm [(\sin^2 A - \tan^2 \psi \cos^2 A) \sin 2\alpha + \tan \psi \cos \Delta \sin 2A \cos 2\alpha] \}$$

for $P = \pm 45° + \alpha$, wherein $\alpha$ is a deviation of azimuth angle of the polarizer, therefore, while $P = 45° + \alpha$ $$\tan^2 \psi = (1-\sin 2\alpha)(1-R \cos 2\beta_0)/(1-\sin 2\alpha)(1+R \cos 2\beta_0) \quad (9)$$

and while $P = 45° + \alpha$ $$\tan^2 \psi = (1+\sin 2\alpha)(1-R' \cos 2\beta')/(1-\sin 2\alpha)(1+R \cos 2\beta') \quad (10)$$

wherein R' and $\beta'$ correspond to factors R and $\beta_0$ in the equation $J(A) = L \cos^2(A-\beta_0) + T \sin^2(A-\beta_0)$, thereafter taking $\beta_{av} = (180-\beta'+\beta_0)/2$, and substituting $\beta_0$ with $\beta_{av}$ to calculate the ellipsometric parameters.

3. The method for measuring ellipsometric parameters as claimed in claim 2 wherein, said step (vi) systematically aligning the polarizer and the analyzer to the plane of incidence of the sample further includes the sub-steps of:

measuring an intensity $I_{a1}$ at a first incident angle while the polarizer azimuth angle P is rotated to 45° and the analyzer azimuth angle A is at the aligned position, measuring an intensity $I_{a2}$ at the first incident angle while the polarizer azimuth angle A is rotated to 45° and the analyzer azimuth angle A is rotated to 90°, measuring an intensity $I_{b1}$ at the first incident angle while the polarizer azimuth angle P is rotated to −45° and the analyzer azimuth angle A is at the aligned position, measuring an intensity $I_{b2}$ at the first incident angle while the polarizer azimuth angle P is rotated to −45° and the analyzer azimuth angle is rotated to 90°, obtaining the azimuthal deviations $\alpha$ and $\beta$ of the polarizer and the analyzer azimuth angles, respectively by deducing the positions of the polarizer and the analyzer corresponding to the plane of incidence according to intensity quotients $\Gamma_a$ and $\Gamma_b$, respectively defined by $$\Gamma_a = I_{a1}(\pi/4\alpha, \beta)/I_{a2}(\pi/4\alpha, \pi/2+\beta) = \tan^2\psi - 2[2 \tan^2\psi \cdot \alpha - \sec^2\psi \cdot \tan \psi \cdot \cos \Delta \cdot \beta)$$

$$\Gamma_b = I_{b1}(-\pi/4+\alpha, \beta)/I_{b2}(-\pi/4+\alpha, \pi/2+\beta) = \tan^2\psi + 2[2 \tan^2\psi \cdot \alpha - \sec^2\psi \cdot \tan \psi \cdot \cos \Delta \cdot \beta)$$

hence, while $\Gamma_a = \Gamma_b$, $$[2 \tan^2\psi \cdot \alpha - \sec^2\psi \cdot \tan \psi \cdot \cos \Delta \cdot \beta] = 0$$

repeating said measuring steps and said obtaining the azimuthal deviations $\alpha$ and $\beta$ step for a second incident angle, so that $\alpha$ and $\beta$ can be calculated by solving simultaneous equations for the first and second incident angles.

* * * * *